US00PP35819P2

(12) United States Plant Patent
Akashi et al.

(10) Patent No.: US PP35,819 P2
(45) Date of Patent: May 21, 2024

(54) ZOYSIAGRASS PLANT NAMED 'SFZ1901'

(50) Latin Name: *Zoysia Willd*
Varietal Denomination: SFZ1901

(71) Applicant: SUMITOMO FORESTRY LANDSCAPING CO., LTD., Tokyo (JP)

(72) Inventors: Ryo Akashi, Miyazaki (JP); Masatsugu Hashiguchi, Miyazaki (JP)

(73) Assignee: SUMITOMO FORESTRY LANDSCAPING CO., LTD., Tokyo (JP)

( * ) Notice: Subject to any disclaimer, the term of this patent is extended or adjusted under 35 U.S.C. 154(b) by 0 days.

(21) Appl. No.: 18/445,116

(22) Filed: Apr. 19, 2023

(30) Foreign Application Priority Data

Nov. 25, 2022 (JP) ..... 36558

(51) Int. Cl.
*A01H 5/12* (2018.01)
*A01H 6/46* (2018.01)

(52) U.S. Cl.
USPC ..... Plt./390
CPC ..... *A01H 6/469* (2018.05)

(58) Field of Classification Search
USPC ..... Plt./390
CPC ..... A01H 6/469; A01H 5/00; A01H 5/12
See application file for complete search history.

*Primary Examiner* — Keith O. Robinson
(74) *Attorney, Agent, or Firm* — Oblon, McClelland, Maier & Neustadt, L.L.P.

(57) ABSTRACT

A new and distinct variety of *Zoysia* Willd. plant named 'SFZ1901' with a unique combination of characteristics including short leaf blade length, slow aboveground parts and stolon elongation rate, longer maintenance of greenness in winter, and management-savings.

3 Drawing Sheets

Latin name of the genus and species of the plant claimed: *Zoysia* Willd.

Variety denomination: 'SFZ1901'.

CROSS-REFERENCE TO RELATED APPLICATION

This application claims the priority of the Japanese Plant Variety Registration Application No. 36558 filed on Nov. 25, 2022, which is incorporated by reference herein as if set forth in its entirety.

BACKGROUND OF THE INVENTION

The present invention relates to a new and distinct perennial *Zoysia* grass cultivar identified as 'SFZ1901' *Zoysia* grass (herein referred to as 'SFZ1901'). 'SFZ1901' was obtained in 2008 from the crossbreeding between the *Zoysia japonica* cultivar 'Asagake' (not patented) (mother plant, Japanese Plant Variety Registration No. 10487) and the wild strain of *Zoysia matrella* (father plant, which had been stored for a long time in Miyazaki-city, Miyazaki-prefecture, Japan, precise origin unknown) in Miyazaki-city, Miyazaki-prefecture, Japan. After germination of the 192 obtained seeds, the inventor selected the 64 $F_1$ individuals in which the crossbreeding was confirmed by *Zoysia* grass-derived SSR marker. The pot trial of the selected 64 $F_1$ individuals was carried out from 2011 to 2018, while maintaining them by vegetative propagation by cutting of stolons. As a result, a stolon elongation rate of one individual of the 64 individuals was found as notably slow, and in 2018, that individual was selected as a candidate of a new variety for registration for protection under the UPOV Convention. After that, the characterization of the selected individual was carried out in the field condition in 2019, and the individual was confirmed as being a new *Zoysia* grass strain with a unique combination of characteristics, including short leaf blade length, slow aboveground parts and stolon elongation rate, longer maintenance of greenness in winter, and management-savings. Subsequently, the characteristics test for Japanese plant variety registration application of the above-identified new *Zoysia* grass strain was carried out from April 2020 to April 2022 in the test field in Miyazaki-city, Miyazaki-prefecture, Japan, and the strain was named 'SFZ1901'. The data on the comparison of the characteristics of 'SFZ1901' with those of 'Asagake' (mother plant) and the wild strain of *Zoysia matrella* (father plant), which was obtained from the characterization of the 'SFZ1901' in 2019, are summarized in the Table 1 below.

TABLE 1

Comparison of the characteristics of 'SFZ1901' with those of parent varieties 'Asagake' (mother plant) and the wild strain of Zoysia matrella (father plant) in October, 2019

| | Plant Height (cm) | Leaf blade length (mm) | Leaf blade width (mm) | Width of stolon (mm) | Internode length of stolon (mm) | Maximum radius of stolon (cm) |
|---|---|---|---|---|---|---|
| Asagake (mother plant) | 14.06 | 96.49 | 5.36 | 2.01 | 32.01 | 33.78 |
| The wild strain of Zoysia matrella (father plant) | 8.17 | 25.00 | 1.84 | 1.14 | 12.81 | 19.67 |
| SFZ1901 | 6.56 | 38.40 | 3.15 | 1.06 | 11.85 | 20.28 |

At the almost same time as the characteristics test, which was carried out from April 2020 to April 2022, the comparison study of traits between 'SFZ1901' and 'Himeno' (U.S. Plant Pat. No. 13,267) (which is the morphologically and physiologically similar variety to 'SFZ1901'), was carried out. 'SFZ1901' is a distinct variety of *Zoysia* Willd., which can be vegetatively propagated by both stolons and rhizomes in Miyazaki-city, Miyazaki-prefecture, Japan, and is uniform in growth expression through successive generations. 'SFZ1901' is the variety denomination of this new *Zoysia* grass. The name 'SFZ1901' may also designate this plant in commerce.

BRIEF SUMMARY OF THE INVENTION

'SFZ1901' is a new and distinct perennial variety of *Zoysia* Willd., which is characterized by a unique combination of characteristics, including:

(1) short leaf blade length;
(2) slow aboveground parts and stolon elongation rate;
(3) longer maintenance of greenness in winter; and
(4) management-savings.

BRIEF DESCRIPTION OF THE FIGURES

The patent or application file contains at least one drawing executed in color. Copies of this patent or patent application publication with color drawing(s) will be provided by the Office upon request and payment of the necessary fee.

COMPLETE DESCRIPTION OF THE VARIETY

Figure 1:
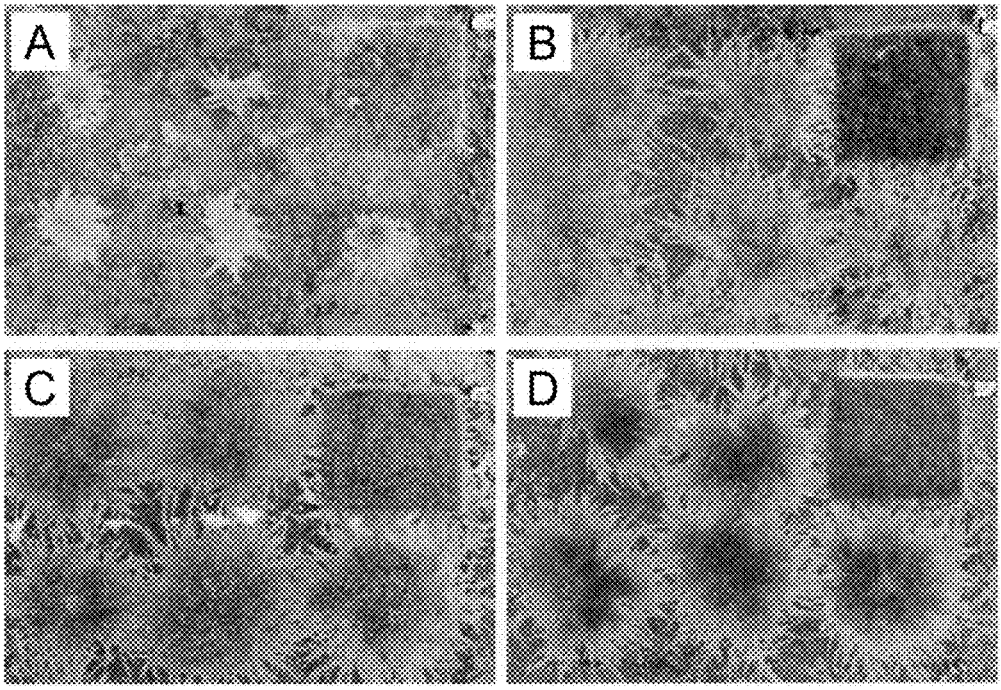
FIG. 1 compares the spread of the aboveground parts of 'SFZ1901', 'Himeno', 'Meyer' (not patented) and 'Emerald' (not patented) (sparse planting zone and close planting zone). Plant ages of each of the four varieties were 13 months old. Photographing date: Jul. 21, 2021. Photographing site: Test field in Miyazaki-city, Miyazaki-prefecture, Japan.

The following is a detailed description of the new *Zoysia* Willd. grass variety known as 'SFZ1901', based upon observations of the plant grown in pots and fields.

'SFZ1901' is a perennial, vegetatively propagated *Zoysia* grass, and is believed to be a unique variety of *Zoysia* Willd. due to its morphological properties. The mother plant of 'SFZ1901' was the *Zoysia japonica* cultivar 'Asagake' (Japanese Plant Variety Registration No. 10487), and the father plant was the wild strain of *Zoysia matrella* (which had been stored for a long time in Miyazaki-city, Miyazaki-prefecture, Japan, precise origin unknown). 'SFZ1901' was obtained from the crossbreeding between 'Asagake' and the above-identified wild strain of *Zoysia matrella*.

The inventor vegetatively propagated 'SFZ1901' by cutting of stolons, and discovered that 'SFZ1901' is a new and distinct variety compared to 'Himeno', 'Meyer' and 'Emerald' (all of which are the morphologically and physiologically similar varieties to 'SFZ1901'). Compared to other *Zoysia* grass varieties, 'SFZ1901' is characterized by its unique combination of characteristics, including shorter leaf blade length, slower aboveground parts and stolon elongation rate, longer maintenance of greenness in winter, and more management-savings.

'SFZ1901' was propagated by cutting of stolons under greenhouse and field conditions in Miyazaki-city, Miyazaki-prefecture, Japan, rooting them in soil, and planting of the rooted material to provide planting stock for studying performance and for comparison of morphological characters after propagation. Asexually reproduced plants of 'SFZ1901' have remained stable and true to type through successive generations of propagation. No seedling establishment from 'SFZ1901' has been noticed in either greenhouse or field studies.

'SFZ1901' is a perennial *Zoysia* grass that spreads by both stolons and rhizomes. Characteristics of 'SFZ1901' measured in 2021 were taken from plants that were approximately 1 to 2 years in age. Both the greenhouse and the test field are located in Miyazaki-city, Miyazaki-prefecture, Japan (USDA Plant Hardiness Zone 9A). The annual minimum temperature in Miyazaki-city, Miyazaki-prefecture, Japan is 3.0 degree Celsius (which corresponds to the average minimum temperature in January in Miyazaki-city), and the annual maximum temperature in Miyazaki-city is 31.6 degree Celsius (which corresponds to the average maximum temperature in August in Miyazaki-city).

The inventor carried out the comparison study of traits between 'SFZ1901' and 'Himeno' (which is the most morphologically and physiologically similar variety to 'SFZ1901') in the test field in Miyazaki-city, Miyazaki-prefecture, Japan, from April 2020 to March 2022. The results of the comparison study are shown in Table 2 below:

TABLE 2

Comparison with a similar variety 'Himeno' (Japanese Plant Variety Registration No. 9209, ZOYSIAN JAPAN CO., LTD.)

| Name of similar variety | Name of trait | Characteristics of the similar variety ('Himeno') | Characteristics of the present variety ('SFZ1901') |
|---|---|---|---|
| Himeno | Leaf blade length | Medium (56.5 mm) | Short (37.0 mm) |
| Himeno | Vigor of early stage | High | Poor |
| Himeno | Regrowth vigor | Medium | Very poor |
| Himeno | Time of greening | Slightly late (March 18) | Very early (February 27) |
| Himeno | Time of coloring (in autumn) | Medium (December 25) | Very late (January 7) |

* The results were confirmed in the test field in Miyazaki-city, Miyazaki-prefecture, Japan.

Figure 2:
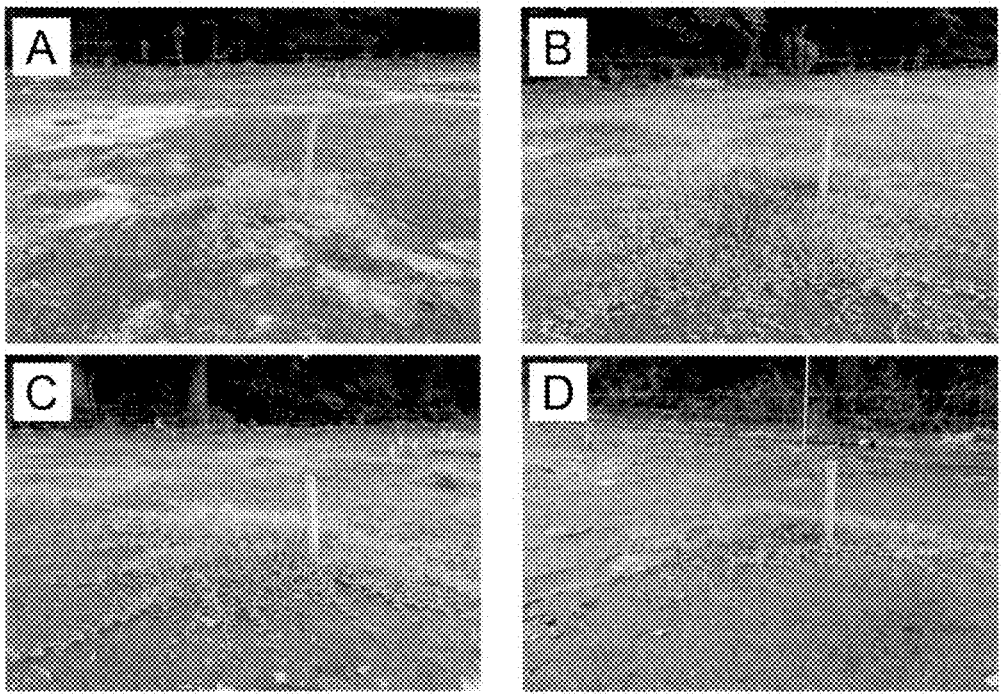
FIG. 2 compares the leaf blade length and the vigor of early stage of 'SFZ1901', 'Himeno', 'Meyer' and 'Emerald'. Plant ages of each of the four varieties were 12 months old. Photographing date: Jun. 14, 2021. Photographing site: Test field in Miyazaki-city, Miyazaki-prefecture, Japan.

As shown in Table 2, the leaf blade length of 'SFZ1901' (37.0 mm) was significantly shorter than that of 'Himeno' (56.5 mm), and the vigor of early stage of 'SFZ1901' was poorer than that of 'Himeno' (see also FIGS. 1 and 2).

Figure 3:
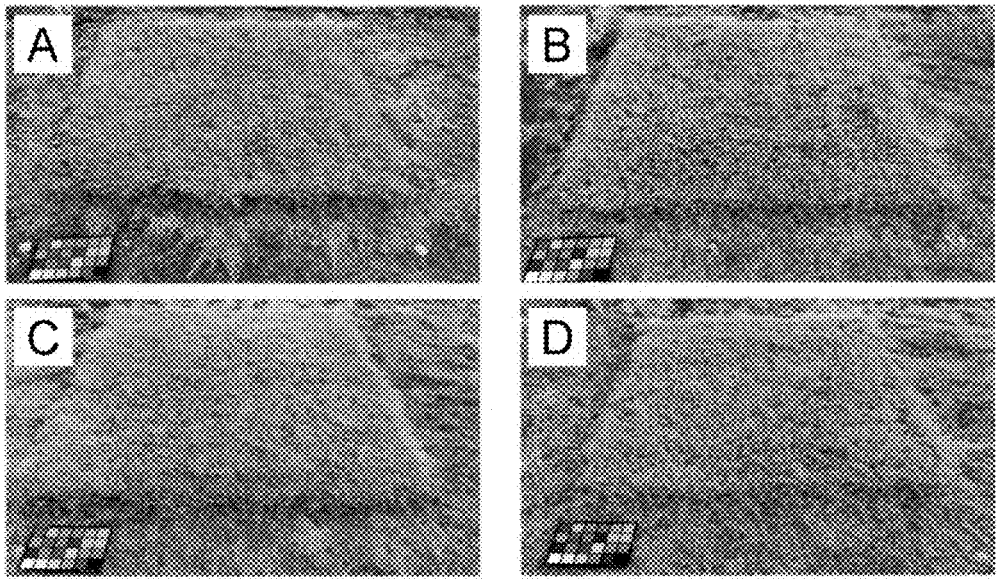
FIG. 3 compares the time of coloring (in autumn) of 'SFZ1901', 'Himeno', 'Meyer' and 'Emerald'. Plant ages of each of the four varieties were 18 months old. Photographing date: Dec. 21, 2021. Photographing site: Test field in Miyazaki-city, Miyazaki-prefecture, Japan.

In addition, the time of greening of 'SFZ1901' (February 27) was significantly earlier than that of 'Himeno' (March 18), and the time of coloring (in autumn) of 'SFZ1901' (January 7) was extremely later than that of 'Himeno' (December 25) (see also FIG. 3). Thus, it can be concluded that 'SFZ1901' has better winter survival ability than 'Himeno'.

When compared to the other two similar varieties, 'Meyer' and 'Emerald', the leaf blade length of 'SFZ1901' (37.0 mm) was also significantly shorter than those of 'Meyer' (60.8 mm) and 'Emerald' (44.2 mm), and the vigor of early stage of 'SFZ1901' was poorer than those of 'Meyer' and 'Emerald' (see FIGS. 1 and 2).

Furthermore, the time of greening of 'SFZ1901' (February 27) was earlier than those of 'Meyer' (March 10) and 'Emerald' (March 6), and the time of coloring (in autumn) of 'SFZ1901' (January 7) was significantly later than that of 'Meyer' (December 13) (see also FIG. 3).

It is apparent from FIGS. 1 and 2 provided herein that 'SFZ1901' in the test field grew at a slower rate than 'Himeno', 'Meyer' and 'Emerald'. The relatively poorer vigor of early stage of 'SFZ1901' than those of 'Himeno', 'Meyer' and 'Emerald', as described above, was due to its slow aboveground parts and stolon elongation rate.

The above results confirm the distinctness of 'SFZ1901' from the other major varieties of *Zoysia* grass.

As described herein above, since 'SFZ1901' has short leaf blade length (37.0 mm) as well as slow aboveground parts and stolon elongation rate, if this variety is used for greening of park, garden or rooftop, or used as home lawn, both frequency and labor of lawn mowing can be reduced, and thus management savings can be achieved.

In addition, as the time of greening of 'SFZ1901' is relatively early (February 27) and the time of coloring is relatively late (January 7), 'SFZ1901' can maintain its greenness for a long time even in winter, so that this variety can maintain its aesthetics relatively longer than other *Zoysia* grass varieties.

Therefore, 'SFZ1901' is considered to be a management-savings type of *Zoysia* grass, and is promising as a suitable and ideal *Zoysia* grass for greening of park, garden or rooftop, and also as home lawn.

BOTANICAL DESCRIPTION OF THE VARIETY

The following is a detailed botanical description of the new variety of *Zoysia* grass 'SFZ1901', based upon observations of 1 to 2 years old specimens grown in Miyazaki-city, Miyazaki-prefecture, Japan, with color notations based on The R.H.S. Color Chart 2015.

1. Plant:
   - *Growth habit*.—Semi-upright.
   - *Vigor of early stage*.—Poor.
   - *Height*.—10.0 cm; 'Himeno': 16.3 cm; 'Meyer': 17.3 cm; 'Emerald': 10.4 cm.
   - *Width*.—105.5 cm; 'Himeno': 288.7 cm; 'Meyer': 267.6 cm; 'Emerald': 261.4 cm.
   - *Density*.—49.5 cm/100 $cm^2$; 'Himeno': 52.3 cm/100 $cm^2$; 'Meyer': 62.4 cm/100 $cm^2$; 'Emerald': 61.8 cm/100 $cm^2$.
2. Stolon:
   - *Anthocyanin coloration of leaf sheath*.—Medium; 'Himeno': strong; 'Meyer': medium; 'Emerald': weak.
   - *Length of leaf sheath*.—19.2 mm; 'Himeno': 22.6 mm; 'Meyer': 23.9 mm; 'Emerald': 28.5 mm
   - *Density of hairiness on leaf sheath*.—Sparse; 'Himeno': sparse; 'Meyer': sparse; 'Emerald': sparse.
   - *Internode length*.—17.9 cm; 'Himeno': 42.2 cm; 'Meyer': 33.8 cm; 'Emerald': 36.0 cm.
   - *Width of internode*.—1.1 mm; 'Himeno': 2.0 mm; 'Meyer': 1.8 mm; 'Emerald': 1.4 mm.
   - *Stolon color*.—60B (color code based on The R.H.S. Color Chart); 'Himeno': 59A; 'Meyer': 60A; 'Emerald': 60A.
3. Culm:
   - *Culm length*.—42.2 mm; 'Meyer': 108.6 mm; 'Emerald': 62.1 mm.
   - *Culm width*.—0.5 mm; 'Meyer': 0.7 mm; 'Emerald': 0.7 mm.
4. Leaf:
   - *Leaf blade length*.—37.0 mm; 'Himeno': 56.5 mm; 'Meyer': 60.8 mm; 'Emerald': 44.2 mm.
   - *Leaf blade width*.—2.8 mm; 'Himeno': 4.2 mm; 'Meyer': 3.6 mm; 'Emerald': 1.9 mm.
   - *Leaf blade intensity of green color*.—138A (color code based on The R.H.S. Color Chart); 'Himeno': 137B; 'Meyer': 137B; 'Emerald': 137C.
   - *Leaf blade density of hairs on upper side*.—Very sparse; 'Himeno': medium; 'Meyer': medium; 'Emerald': medium.
   - *Leaf blade density of hairs on lower side*.—Very sparse; 'Himeno': very sparse; 'Meyer': very sparse; 'Emerald': very sparse.
   - *Leaf blade margin*.—Smooth; 'Himeno': smooth; 'Meyer': smooth; 'Emerald': smooth.
   - *Leaf sheath density of hairs*.—Sparse; 'Himeno': sparse; 'Meyer': sparse; 'Emerald': sparse.
   - *Shape of ligule*.—Fringe of hairs; 'Himeno': fringe of hairs; 'Meyer': membranous; 'Emerald': fringe of hairs.
5. Flag leaf:
   - *Flag leaf length*.—9.1 cm; 'Meyer': 16.6 cm; 'Emerald': 9.3 cm.
   - *Flag leaf width*.—0.7 cm; 'Meyer': 1.6 cm; 'Emerald': 0.9 cm.
6. Inflorescence:
   - *Inflorescence length*.—21.8 mm; 'Meyer': 28.7 mm; 'Emerald': 17.4 mm.
   - *Inflorescence width*.—0.8 mm; 'Meyer': 1.5 mm; 'Emerald': 1.0 mm.
   - *Color of spikelets*.—60A (color code based on The R.H.S. Color Chart); 'Meyer': 59A; 'Emerald': 59A.
   - *Length of spikelets*.—3.1 mm; 'Meyer': 3.2 mm; 'Emerald': 3.1 mm.
   - *Width of spikelets*.—0.9 mm; 'Meyer': 1.1 mm; 'Emerald': 0.9 mm.
   - *Number of spikelets*.—13.7; 'Meyer': 34.8; 'Emerald': 19.7.
7. Others:
   - *Time of greening*.—February 27; 'Himeno': March 18; 'Meyer': March 10; 'Emerald': March 6.
   - *Time of flowering* (*in spring*).—March 19; 'Meyer': March 5; 'Emerald': March 17.
   - *Time of coloring of leaves* (*in autumn*).—January 7; 'Himeno': December 25; 'Meyer': December 13; 'Emerald': January 9.
   - *Intensity of anthocyanin coloration* (*in autumn*).—Slightly weak; 'Himeno': very weak; 'Meyer': weak; 'Emerald': very weak.

What is claimed is:

1. A new and distinct variety of *Zoysia* Willd. plant named 'SFZ1901', substantially as described and illustrated herein.

* * * * *

Comparison of each varieties (aerial photo), photographed on July 21, 2021, in the test field of the Field Science Center, attached to the Faculty of Agriculture of University of Miyazaki (Miyazaki city, Miyazaki prefecture, Japan)

A: SFZ1901
B: Himeno
C: Meyer
D: Emerald

Comparison of each varieties, photographed on June 14, 2021, in the test field of the Field Science Center, attached to the Faculty of Agriculture of University of Miyazaki (Miyazaki city, Miyazaki prefecture, Japan)

A: SFZ1901
B: Himeno
C: Meyer
D: Emerald

Comparison of each varieties (aerial photo), photographed on December 21, 2021, in the test field of the Field Science Center, attached to the Faculty of Agriculture of University of Miyazaki (Miyazaki city, Miyazaki prefecture, Japan)

A: SFZ1901
B: Himeno
C: Meyer
D: Emerald